United States Patent [19]

McCombs

[11] Patent Number: 6,103,943
[45] Date of Patent: Aug. 15, 2000

[54] PREPARATION OF 3-BUTEN-1-OL FROM 3,4-EPOXY-1-BUTENE

[75] Inventor: Charles Allan McCombs, Kingsport, Tenn.

[73] Assignee: Eastman Chemical Company, Kingsport, Tenn.

[21] Appl. No.: 09/009,345

[22] Filed: Jan. 20, 1998

[51] Int. Cl.⁷ .................... C07C 29/10; C07C 33/025
[52] U.S. Cl. ............... 568/908; 568/907; 568/909.5; 568/900
[58] Field of Search ................... 564/477, 474, 564/475, 487, 503, 509; 568/695, 908, 909.5, 900, 907; 585/520; 524/113, 709; 562/609; 502/200, 213

[56] References Cited

U.S. PATENT DOCUMENTS

| | | | |
|---|---|---|---|
| 3,574,773 | 4/1971 | Mueller | 568/879 |
| 4,261,901 | 4/1981 | Squire | 549/429 |
| 4,288,374 | 9/1981 | Squire | 568/879 |
| 5,288,910 | 2/1994 | Hung | 564/477 |
| 5,326,873 | 7/1994 | Godleski et al. | 544/401 |
| 5,401,888 | 3/1995 | Larock | 568/907 |
| 5,406,007 | 4/1995 | Falling | 568/908 |
| 5,600,034 | 2/1997 | Mori et al. | |

OTHER PUBLICATIONS

J. Tsuji et al., Chem. Letters, 1017 (1984).
J. Tsuji et al., Tetrahedron Letters, No. 7, pp. 613–616 (1979).

*Primary Examiner*—Michael P. Woodward
*Assistant Examiner*—Marjoeie A. Moran
*Attorney, Agent, or Firm*—Michael J. Blake; Harry J. Gwinnell

[57] ABSTRACT

Disclosed is a process for the synthesis of 3-buten-1-ol by contacting 3,4-epoxy-1-butene and formic acid with a homogeneous catalyst solution comprising a palladium(0) compound, a tertiary phosphine and a trialkylamine dissolved in tetrahydrofuran.

7 Claims, No Drawings

PREPARATION OF 3-BUTEN-1-OL FROM 3,4-EPOXY-1-BUTENE

This invention pertains to a process for the preparation of 3-buten-1-ol from 3,4-epoxy-1-butene (EpB). More specifically, this invention pertains to the synthesis of 3-buten-1-ol by contacting EpB and formic acid with a catalyst solution comprising a palladium(0) compound, a tertiary phosphine and a trialkylamine dissolved in tetrahydrofuran (THF).

U.S. Pat. No. 3,574,773 discloses the preparation of 3-buten-1-ol by reacting propylene with aqueous formaldehyde in the presence of a base such as ammonia at a temperature of 235 to 400° C. and a pressure of 50 to 500 atmospheres. U.S. Pat. Nos. 4,261,901 and 4,288,374 also describe the preparation of 3-buten-1-ol by reacting propylene and aqueous formaldehyde stabilized with an alcohol in the presence of silica sand at a temperature of 250 to 350° C. and a pressure of 50 to 800 atmospheres. A 27% conversion of formaldehyde to 3-buten-1-ol is reported in an example.

U.S. Pat. No. 5,406,007 discloses a process for preparing a mixture of 2-buten-1-ol (crotyl alcohol) and 3-buten-1-ol by the hydrogenation of EpB in the presence of a sulfur-modified or sulfided nickel catalyst. J. Tsuji et al., *Chem. Letters,* 1017 (1984) disclose the preparation of 3-buten-1-ol by heating a mixture of tris(dibenzylideneacetone)dipalladium(0)-chloroform adduct, tributylphosphine and ammonium formate and dioxane solvent at 100° C. for 1 hour. The use of the Tsuji et al. process to manufacture 3-buten-1-ol on a commercial scale is not practical because of the toxicity of the chloroform and dioxane (a suspected carcinogen) and the production of a white solid during the operation of the process. This white solid is believed to be a mixture of ammonium formate and a carbamic acid formed from ammonia and carbon dioxide derived from the ammonium formate. The white solid can foul and plug process equipment such as condensers which may lead to hazardous situations due, in part, to the generation of carbon dioxide and ammonia from the decomposition of ammonium formate during operation of the process. As ammonia and carbon dioxide gases are generated, the pressure within the reactor can build up, resulting in a catastrophic failure of the equipment. This plugging problem is a serious safety problem that prevents the Tsuji et al. process from being used in a commercial-scale manufacturing process.

A process now has been developed which permits the safe manufacture of 3-buten-1-ol from EpB on a commercial scale. In process of the present invention, EpB is converted to 3-buten-1-ol by contacting EpB and formic acid with a catalyst solution comprising a palladium(0) compound, a tertiary phosphine and a trialkylamine dissolved in THF. Replacing the ammonium formate used by Tsuji et al. with a mixture of a high-boiling amine such as tri-n-butylamine and formic acid eliminates the plugging problem and cause the reaction mixture to become homogeneous. The Tsuji et al. process is heterogeneous due to the limited solubility of ammonium formate in dioxane. The homogeneous reaction mixture involved in the process of the present invention causes the reaction rate to be accelerated significantly. This rate acceleration enables (1) the trialkylamine to be used in catalytic amounts, (2) a substantial reduction in the amount of palladium catalyst and (3) four times the amount of EpB to be added (with reference to the Tsuji et al. process) to produce 3-buten-1-ol, provided enough formic acid is present, using 22% less palladium catalyst. The present invention, therefore, provides a process for the preparation of 3-buten-1-ol by contacting EpB and formic acid in a homogeneous catalyst solution comprising a palladium(0) compound, a tertiary phosphine and a trialkylamine dissolved in THF.

The particular THF-soluble palladium(0) compound used is not critical and can be selected from various palladium(0) complexes such as tris(dibenzylideneacetone)dipalladium(0) and tetrakis(trialkylphosphine)palladium(0). The palladium(0) is present in the THF catalyst solution in a catalytic amount, e.g., from about 0.005 to 0.5 weight percent Pd. Palladium concentrations of about 0.01 to 0.1 weight percent are preferred.

The tertiary (trisubstituted) phosphine may be selected from a wide variety of trihydrocarbylphosphines wherein the total carbon content of the 3 hydrocarbyl (or hydrocarbon) groups, e.g., alkyl, cycloalkyl and aryl groups, ranges from about 3 to 30 carbon atoms. The tertiary phosphine preferably is selected from trialkylphosphines wherein the total carbon content of the 3 alkyl groups is in the range of about 8 to 15. Tri-n-butylphosphine is the phosphine used in the examples presented herein and therefore is particularly preferred. The amount of phosphine used in the present process should be an amount which gives a P:Pd atomic ratio of at least 1.00, preferably at least 3.00. Preferred phosphine concentrations provide P:Pd atomic ratios in the range of about 1.80 to 1.95.

The trialkylamine normally employed in the process is selected from trialkylamines containing a total of about 3 to 30 carbon atoms (total carbon atom content of the 3 alkyl groups), preferably about 12 to 15. In addition, for convenience in distilling the product, the trialkylamine may have a boiling point of at least 180° C. Specific examples of trialkylamines which may be used in the process include tri-n-butylamine, dioctyl (methyl) amine, dimethyl(octyl) amine, tri-n-octylamine, and dicyclohexyl(ethyl)amine. The concentration of the trialkylamine in the THF catalyst solution may be in the range of about 10 to 50 weight percent, preferably about 20 to 25 weight percent, based on the total weight of the catalyst solution.

The formic acid used in the process may be provided as an aqueous solution of formic acid or as essentially pure formic acid, e.g., from about 70 to 100 weight percent formic acid. The water which is introduced into the system when an aqueous, formic acid solution is used does not affect the catalyst system or its activity. However, for the purpose of product purification and avoiding or minimizing the formation of product/water azeotropes, the amount of water present in the reaction mixture preferably is minimized, e.g., by using an aqueous, formic acid solution comprising at least 90, preferably at least 95, weight percent formic acid.

The process is operated at elevated temperatures, typically at least 55° C. and preferably up to the boiling point of the reaction mixture. The process may be carried out at pressures moderately above or below atmospheric but normally is carried out at ambient pressure or the autogenous pressure generated within the process equipment.

The process provided by the present invention may be carried out by first forming a solution comprising the catalyst components (palladium, trialkylphosphine and trialkylamine), formic acid and THF and then adding the EpB either slowly and/or in increments to the solution. Alternatively and preferably, the EpB and the formic acid are added separately, slowly and/or incrementally, to a solution of the catalyst components in THF. Normally, the amounts of EpB and formic acid used over the course of the process are approximately equimolar.

The product obtained from the process of this invention is 3-buten-1-ol and 2-buten-1-ol (cis and trans) produced in a ratio of about 90:10. Crotonaldehyde, resulting from isomerization of EpB, is the major product impurity (10–20%) along with minor amounts of n-butanol and butenyl formate. Although Tsuji et al. do not report the presence of crotonaldehyde in the product they obtained, it is probable that crotonaldehyde was formed by Tsuji et al. but quickly reacted with ammonia to form imines. Such imine formation is evidenced by the presence of high boilers in the product obtained by Tsuji et al. In the process of the invention, the tertiary trialkylamine cannot react with crotonaldehyde and, thus, crotonaldehyde is observed in the product. This conclusion may be demonstrated by performing my novel process using a primary or secondary amine instead of a trialkylamine. Primary and secondary amines can form an imine with crotonaldehyde and, as expected, crotonaldehyde was not observed as a reaction product and high boilers were present.

Since crotonaldehyde cannot easily be separated from 3-buten-1-ol by distillation, product isolation may be assisted by the addition of a primary or secondary amine to the reaction mixture when the process has been completed. Such a primary or secondary amine will react with crotonaldehyde to form a high-boiling imine compound which is readily separable from the butenol product. Morpholine has been found to be particularly effective in converting by-product crotonaldehyde to a high-boiling imine. Crotonaldehyde separation also can be accomplished by the addition of an alkali metal hydroxide or carbonate, e.g., sodium hydroxide, to the reaction mixture to convert the crotonaldehyde to its dimer via an aldol condensation reaction. However, this reaction is slower than the reaction with morpholine and the addition of an alkali metal hydroxide or carbonate can cause product quality problems.

At the conclusion of the process, the catalyst may be inactivated, if desired, e.g., for recovery of the 3-buten-1-ol product, by the addition of 30% hydrogen peroxide and/or cupric chloride to minimize isomerization of 3-buten-1-ol to 2-buten-1-ol. The addition of either material permits distillation of the product from high boilers and the palladium catalyst without further isomerization to 2-buten-1-ol. When the process is operated on a larger scale, cupric chloride is the preferred method because it oxidizes and inactivates the palladium catalyst.

The process of the present invention is further illustrated by the following examples. Analytical results were determined by means of conventional gas chromatography procedures.

EXAMPLE 1

Tributylamine (78 ml, 0.37 mole) and formic acid (70 g of 88% pure formic acid, 1.339 mole) were added to 300 mL of THF solvent at room temperature. Tris(dibenzylideneacetone)dipalladium(0) (0.32 g, 0.35 millimole) and tributylphosphine (0.9 ml, 3.6 mmole) are added to the above mixture and the temperature is raised to 60° C. EpB (105 mL, 1.257 mole) is added dropwise over a period of about 2 hours and the mixture quickly heats up to reflux temperature (about 72° C.).

After about 3 to 3.5 hrs, the reaction is complete, and the color of the reaction mixture changes to a light green. Hydrogen peroxide (0.25 ml of 35% $H_2O_2$) is added to deactivate the catalyst, and the mixture is assayed for crotonaldehyde content. Based on this assay, an equivalent amount of morpholine is added and the THF and product are distilled from the reaction mixture. The solvent is removed through a fractionating column and the product boils at 112–113° C. The product is a mixture of 3-buten-1-ol and 2-buten-1-ol which is isolated in 65–75% yield after distillation. The major product is 3-buten-1-ol with a selectivity of 88–93%.

EXAMPLE 2

Tributylamine (78 mL) and formic acid (30 mL of 96% aqueous formic acid solution) are added to 300 mL of THF solvent in a 1-liter, three-neck flask equipped with an overhead stirrer and a reflux condenser with a dry ice trap above condenser. The addition of formic acid causes an exothermic reaction and the heat generated is used to warm the reaction mixture to the reaction temperature. Tributylphosphine (0.90 mL) and butylated hydroxytoluene (0.10 g) are added followed by the addition of the tris-(dibenzylideneacetone)dipalladium(0) catalyst (0.26 g) is added to prepare the catalyst system. EpB (75 mL) is added dropwise over 1.5 hours, starting when the temperature reaches 60° C. The reaction mixture is refluxed for 30–40 minutes to consume the EpB.

Another 32 mL portion of formic acid is added dropwise quickly, but not all at once. Another 60 mL portion of EpB is added dropwise over 1 hour and the reaction is allowed to take place over a 30–40 minute time period to consume the EpB. This sequential addition of 32 mL of formic acid and 60 ml of EpB followed by a reaction period to consume the EpB was repeated three more times. When the reaction is finished and while the reaction mixture is hot, cupric chloride (0.30 g) and the required amount of morpholine are added. The reaction mixture is distilled through a fractionating column to remove THF and water. The distillation can begin immediately after morpholine addition. Tributylamine and tributylphosphine do not distill from the flask.

The initial product of distillation is the THF/water azeotrope (bp=62° C.) which contains about 3% water. All of the water present in the reaction flask preferably is removed as a component of the THF/water azeotrope to avoid formation of the 3-buten-1-ol/water azeotrope (bp=91° C.). A forecut fraction typically is collected between 70 and 112° C. and the product is obtained as a constant boiling fraction boiling at 112° C. The product is a mixture of 3-buten-1-ol and 2-buten-1-ol which is isolated in a yield of about 60–70%.

COMPARATIVE EXAMPLE 1

EpB (6.0 mL), ammonium formate (6.7 g), tris(dibenzylideneacetone)dipalladium(0) (0.10 g), trioctylphosphine (0.10 mL) were added to 50 ml of THF solvent. This mixture was stirred at reflux for 1 hour and then filtered through silica gel to remove the palladium catalyst. After removing tetrahydrofuran solvent, the product consisted of 3-buten-1-ol/2-buten-1-ol in a mole ratio of >98:2), a small amount of crotonaldehyde, and a large amount of high boilers.

COMPARATIVE EXAMPLE 2

EpB (30.0 mL), ammonium formate (24 g), tris(dibenzylideneacetone)dipalladium(0) (0.15 g) and tributylphosphine (0.50 mL) were added to 50 mL of THF solvent. This mixture was stirred at reflux for 1 hour and then filtered through silica gel to remove the palladium catalyst. The product was analyzed by GC and found to be nearly identical to the product obtained in Comparative Example 1 using trioctylphosphine, which consisted of 3-buten-1-ol/2-buten-1-ol in a mole ratio of >98:2), a small amount of crotonaldehyde, and a large amount of high boilers. This product was distilled through a Vigreux column to afford a product cut with 97.2% selectivity. The isolated yield was 62%. Formation of a white solid during this reaction resulted in a pressure buildup and a vapor release.

The invention has been described in detail with particular reference to preferred embodiments thereof, but it will be understood that variations and modifications can be effected within the spirit and scope of the invention.

I claim:

1. A process for the preparation of 3-buten-1-ol which comprises contacting 3,4-epoxy-1-butene with formic acid in a homogeneous catalyst solution comprising a palladium(0) compound, a tertiary phosphine and a trialkylamine dissolved in tetrahydrofuran (THF).

2. The process according to claim 1 wherein 3,4-epoxy-1-butene is added slowly or incrementally to a solution of formic acid in a homogeneous catalyst solution comprising a palladium(0) compound, a tertiary phosphine and a trialkylamine dissolved in THF at a temperature of about 55° C. to the boiling point of the reaction mixture; wherein the total carbon content of the tertiary phosphine is about 3 to 30 carbon atoms and the total carbon content of the trialkylamine is about 3 to 30.

3. The process according to claim 1 wherein 3,4-epoxy-1-butene and formic acid are added separately, slowly or incrementally, to a homogeneous catalyst solution comprising a palladium(0) compound, a tertiary phosphine and a trialkylamine dissolved in THF at a temperature of about 55° C. to the boiling point of the reaction mixture; wherein the total carbon content of the tertiary phosphine is about 3 to 30 carbon atoms and the total carbon content of the trialkylamine is about 3 to 30.

4. A process for the preparation of 3-buten-1-ol which comprises adding 3,4-epoxy-1-butene slowly or incrementally to a solution of formic acid in a homogeneous catalyst solution comprising a palladium(0) compound, a trialkylphosphine and a trialkylamine dissolved in tetrahydrofuran (THF) at a temperature of about 55° C. to the boiling point of the reaction mixture; wherein (1) the amount of trialkylphosphine present gives a P:Pd atomic ratio of at least 1.00, (2) the total carbon content of the trialkylphosphine is about 8 to 15 carbon atoms, (3) the concentration of the trialkylamine in the THF catalyst solution is about 10 to 50 weight percent, and (4) the total carbon content of the trialkylamine is about 3 to 30.

5. The process according to claim 4 wherein (1) the amount of trialkylphosphine present gives a P:Pd atomic ratio of about 1.80 to 1.95, (2) the concentration of the trialkylamine in the THF catalyst solution is about 20 to 25 weight percent, (3) the total carbon content of the trialkylamine is about 12 to 15, and (4) the concentration of the palladium(0) in the THF catalyst solution is about 0.01 to 0.1 weight percent Pd.

6. A process for the preparation of 3-buten-1-ol which comprises adding 3,4-epoxy-1-butene and formic acid separately, slowly or incrementally, to a homogeneous catalyst solution comprising a palladium(0) compound, a trialkylphosphine and a trialkylamine dissolved in tetrahydrofuran (THF) at a temperature of about 55° C. to the boiling point of the reaction mixture; wherein (1) the amount of trialkylphosphine present gives a P:Pd atomic ratio of at least 1.00, (2) the total carbon content of the trialkylphosphine is about 8 to 15 carbon atoms, (3) the concentration of the trialkylamine in the THF catalyst solution is about 10 to 50 weight percent, and (4) the total carbon content of the trialkylamine is about 3 to 30.

7. The process according to claim 6 wherein (1) the amount of trialkylphosphine present gives a P:Pd atomic ratio of about 1.80 to 1.95, (2) the concentration of the trialkylamine in the THF catalyst solution is about 20 to 25 weight percent, (3) the total carbon content of the trialkylamine is about 12 to 15, and (4) the concentration of the palladium(0) in the THF catalyst solution is about 0.01 to 0.1 weight percent Pd.

* * * * *